Nov. 6, 1934. M. KATZMAN Re. 19,367

ELECTRIC VAPORIZER

Original Filed May 1, 1929

INVENTOR.
Max Katzman

BY
Denison & Thompson
ATTORNEYS

WITNESS
J. T. Maine

UNITED STATES PATENT OFFICE 19,367

ELECTRIC VAPORIZER

Max Katzman, Utica, N. Y.

Original No. 1,879,297, dated September 27, 1932, Serial No. 359,551, May 1, 1929. Application for reissue August 14, 1934, Serial No. 739,835

10 Claims. (Cl. 219—40)

Figure 1:
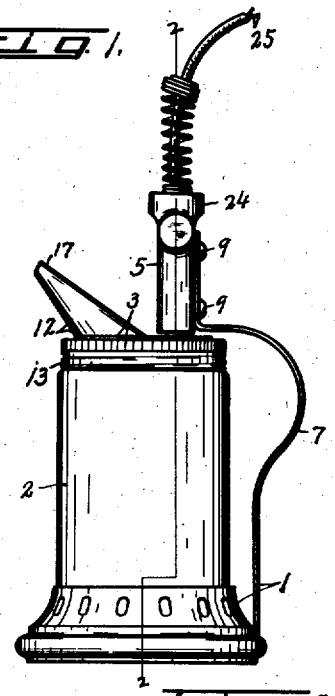

This invention relates to an electric vaporizer of the class set forth in my reissue application Serial No. 220,617, filed September 19th, 1927, original Patent No. 1,628,784, and also my Patents No. 1,927,316, September 19th, 1933, and No. 1,802,654, April 28th, 1931.

The primary object of these devices is to provide a safe and convenient means for electrically vaporizing medicinal and deodorizing liquids and liberating the vapor into the room in which the device is located for hygienic purposes, but obviously is adapted for many other uses, such for example, as humidors for supplying extra moisture to the air in the room.

The present invention, however, relates more particularly to the construction of the electrodes of the heater and to the manner of mounting the same upon the lid or cover of the receptacle, the object being to prolong the life and to greatly increase the heating efficiency of the electrodes and at the same time to reduce the liability of short circuiting deposits upon and between the electrodes by allowing any foreign matter which may accumulate in and around the electrodes to drop by its own weight or by the ebullition of the liquid in the receptacle to the bottom of the container away from the electrodes.

Another object is to hold the electrodes in spaced relation to the lid or cover of the receptacle by means of a spacing block of insulating material having means for holding the adjacent faces of the electrodes in parallel spaced relation to form an intervening liquid-receiving space through which the electric current is adapted to pass for heating the liquid.

In the drawing:

Figure 1 is a side elevation of an electric vaporizer embodying the various features of my invention.

Figure 2:
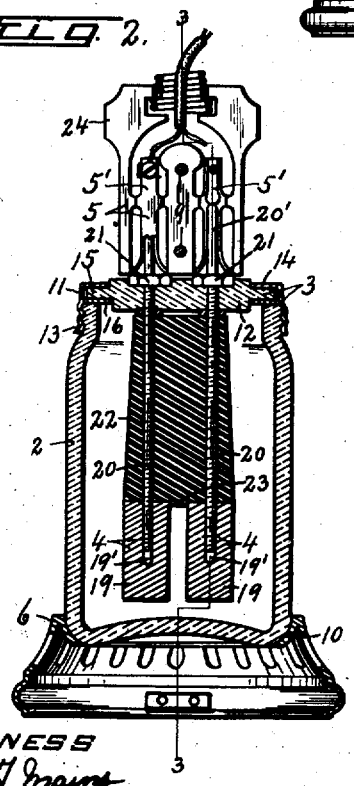
Figure 3:
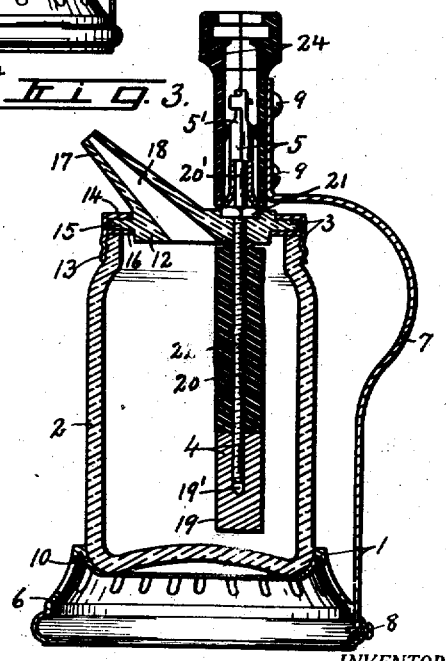

Figures 2 and 3 are enlarged vertical sectional views taken respectively in the planes of lines 2—2, Figure 1, and 3—3, Figure 2.

As illustrated, this device comprises a main supporting frame 1, a receptacle 2 having a removable lid or cover 3, an electric heater 4 and an electric plug or coupler 5.

The frame 1 comprises a circular base 6 and a resilient arm 7 extending upwardly along the outside of the receptacle 2 and having its lower end secured at 8 to the base 6 and its upper end extended above the adjacent portion of the lid 3 and secured by screws 9 or equivalent fastening means to the electric plug or coupler 5.

The base 6 is preferably made of sheet metal and is provided in its upper side with a relatively shallow circular recess 10 in which the lower end of the receptacle is removably seated. The receptacle 2 is preferably made of transparent glass or other suitable insulating material and is adapted to receive the liquid to be vaporized, said receptacle being mainly cylindrical for convenience of handling and cleansing.

The lid or cover 3 preferably comprises a metallic rim or ring section 11 and an insulating section 12 of porcelain or other suitable insulating material. The rim section 3 is preferably angular in cross section to form vertical and horizontal flanges 13 and 14, the flange 13 being preferably threaded to engage corresponding peripheral threads on the upper end of the receptacle 2 while the horizontal flange 14 serves as a means for holding the insulating section 12 in operative position on the upper end of the receptacle.

That is, the insulating section 12 is provided with an annular flange 15 which is adapted to be interposed between the horizontal flange 14 of the rim 11 and end face of the receptacle 2 with a suitable interposed packing 16 to reduce the liability of leakage of the liquid or vapor from the bottle through the adjacent joint.

The insulating section 12 is also provided with an upwardly and laterally extending discharge nozzle 17 having an outlet passage 18 therethrough for the discharge of the vaporized fluid into the room in which the device is located, said outlet being preferably tapered toward its outer end to cause the vapor to be discharged with increased force some distance therefrom into the room.

The heater 4 is suspended from the insulating section 12 of the lid 3 into the interior of the receptacle 2 for submergence into the liquid to be vaporized and comprises, in this instance, a pair of similar rectangular electrodes 19 preferably of steel or other suitable metal and a pair of conductor rods 20 having their upper ends extended through corresponding apertures in the insulating section 12 and provided with external terminal extensions 20′ adapted to be engaged by socketed terminals 5′ of the plug or cover 5.

These terminal rods are provided at their junctions with the terminals 20′ with shoulders 21 normally seated in corresponding recesses in the upper face of the insulating section 12 to hold the rods 20 against downward movement.

These conductor rods 20 are extended downwardly from the lid or cap 3 through corresponding openings in a spacing block 22 of insulating material and having their lower ends threaded and engaged with correspondingly threaded sockets 19′ in the electrodes 19 which obviously permits both electrodes to be reversed about the axes of their respective loads 20 to present different faces thereof to the intervening gap when said faces become impaired.

This insulating block 20 is common to both of the electrodes 19 and extends from the underside of the insulating section 12 to the upper faces of the electrodes to hold the latter in proximity to but slightly above the bottom of the receptacle 2.

The lower end of the insulating block 22 is provided with a relatively narrow rib 23 at right angles to the plane of the conductor rods 20 and adapted to extend a relatively short distance below the upper faces of the electrodes 19 for holding them in uniformly spaced parallel relation for the reception of the liquid to be heated.

The electric plug or coupler 5 comprises the terminal sockets 5′ and an insulating housing 24 therefrom. The terminal sockets 5′ are connected by a suitable cable or conductor 25 to any available source of current supply for the heater electrode 19.

The insulating block 22 is preferably made solid or in one piece of porcelain or other heat-refracting material capable of withstanding the relatively high temperature and moisture within the container 2 without deterioration.

The all-metal electrodes 19 constitute electric conductors of comparatively low electrical resistance so that the electric current which is supplied thereto through the conductors 20 when the terminals 20′ are engaged by the electric plug 5 may readily pass from one electrode to the other through the intervening body of liquid where the greatest ebullition takes place the heat from the electrodes is transmitted to the surrounding liquid throughout the areas thereof to further expedite the conversion of the liquid in the vapor.

One of the important advantages in making the electrodes of metal is that their adjacent faces may be made comparatively smooth and owing to the fact that the space between the electrodes is open at the bottom and at opposite sides, it is evident that any foreign matter which may tend to accumulate therein may readily be precipitated therefrom to the bottom of the receptacle.

Furthermore, the agitation and circulation of the liquid produced by ebullition thereof between the electrodes serves to clean the adjacent faces thereof from any foreign matter thereby increasing the efficiency of the heater in the more rapid conversion of the liquid into vapor. It is obvious upon reference to Figures 2 and 3 that when the plug 5 is removed the threaded connections between the terminal rods 20 and electrodes 19 may be loosened by simply unscrewing the rods sufficiently to permit the electrodes to be turned about the axes of their respective rods to present different faces thereof to the intervening gap in case said faces should become impaired.

What I claim is:

1. In an electric vaporizer, a receptacle having a removable lid provided with a section of insulating material, an electric heater having electric conductors suspended from said insulating section of the lid, said conductors having their upper ends provided with outwardly projecting terminals adapted to receive an electric plug, and metal electrodes secured to the lower ends of the conductors in transversely spaced relation, the spaces between the electrodes being open at the bottom and at opposite sides and an insulating block interposed between the electrodes and underside of the lid and having its lower end provided with a rib projecting a relatively short distance into the space between the electrodes for holding the latter against turning movement.

2. In an electric vaporizer, a receptacle having a removable lid and an electric heater suspended from said lid within the receptacle and comprising a pair of rectangular electrodes having threaded sockets and threaded conductors engaged in said sockets and extending through openings in the lid, said conductors being provided with external terminals adapted to be engaged by an electric plug, and a socketed insulating block of heat-refracting material interposed between the lower face of the lid and upper face of the electrodes and enclosing the adjacent portions of the conductors, said insuating block having its lower end extended a relatively short distance between the electrodes for holding the latter against turning movement of their respective conductors.

3. In an electric vaporizer, a container for the material to be vaporized, an insulating block, a pair of electrodes abutting against the lower end of the block to form an intervening space open at the bottom, and means supported from the top of the container and extending through said block for clamping the electrodes to the lower end thereof.

4. An electric vaporizer comprising a receptacle for the liquid to be vaporized, a lid for the receptacle, electric heater terminals on the lid, conducting rods suspended from the terminals, and electrodes supported by the rods in spaced relation to form an intervening water-gap open at the bottom and at opposite sides.

5. In an electric vaporizer, a receptacle for the liquid to be vaporized, a cover for the receptacle, and an electric heater suspended from the cover and provided at its lower end with electrodes in spaced relation and the space open at the bottom to allow any sediment which may tend to accumulate in the space to precipitate to the bottom of the receptacle away from the electrodes.

6. In an electric vaporizer, a receptacle for the liquid to be vaporized, a cover for the receptacle, conductors suspended from the cover within the receptacle, electrodes mounted on the lower ends of the conductors in transversely spaced relation and having their adjacent faces substantially flat and rectangular, the space between said electrodes being open at the bottom to allow precipitation of sediment therefrom to the bottom of the receptacle, and insulation inclosing the conductors and extending from the electrodes to the cover.

7. In an electric vaporizer, a receptacle for the liquid to be vaporized, a cover for the receptacle, conductors suspended from the cover within the receptacle, electrodes mounted on the lower ends of the conductors in transversely spaced relation and having their adjacent faces substantially flat and rectangular and parallel, the space between said electrodes being open at the bottom to allow precipitation of sediment therefrom to the bottom of the receptacle, and insulating means projecting into the upper portion of said space and engaging the electrodes to hold them in spaced relation.

8. In an electric vaporizer, a receptacle for the liquid to be vaporized, a cover for the receptacle, conductors suspended from the cover within the receptacle, electrodes mounted on the lower ends of the conductors in transversely spaced relation, and insulating means mounted on the conductors above the electrodes for holding them in spaced relation, portions of said insulating means projecting below the upper edge of the electrodes for preventing them from turning.

9. In an electric vaporizer, a receptacle for the liquid to be vaporized, a cover for the receptacle, conductors suspended from the cover within the receptacle, electrodes mounted on the lower ends of the conductors near the bottom of the receptacle, said electrodes being held in transversely spaced relation and having their adjacent faces substantially flat, rectangular and parallel, the space between said electrodes being open at the bottom to allow precipitation of sediment therefrom to the bottom of the receptacle, and insulating means engaging the electrodes to retain them against being turned.

10. In an electric vaporizer, a receptacle for the liquid to be vaporized, a cover for the receptacle, conductors suspended from the cover within the receptacle, electrodes mounted on the lower ends of the conductors near the bottom of the container, insulating means mounted on the conductors between the cover and the electrodes, portions of said insulating means projecting downwardly in engaging relationship with the electrodes to prevent them from turning.

MAX KATZMAN.